(12) United States Patent
Cutkosky et al.

(10) Patent No.: US 8,491,665 B2
(45) Date of Patent: Jul. 23, 2013

(54) SKIN STRETCH TACTILE FEEDBACK DEVICE

(75) Inventors: Mark R Cutkosky, Palo Alto, CA (US); Karlin Y Bark, Mountain View, CA (US); Jason Wheeler, Albuquerque, NM (US); Joan Savall, Palo Alto, CA (US)

(73) Assignees: Sandia Corporation, Albuquerque, NM (US); The Board of Trustees of the Leland Stanford Junior University, Palo Alto, CA (US)

( * ) Notice: Subject to any disclaimer, the term of this patent is extended or adjusted under 35 U.S.C. 154(b) by 562 days.

(21) Appl. No.: 12/639,427

(22) Filed: Dec. 16, 2009

(65) Prior Publication Data

US 2010/0161079 A1    Jun. 24, 2010

Related U.S. Application Data

(60) Provisional application No. 61/203,455, filed on Dec. 22, 2008.

(51) Int. Cl.
*A61F 2/70* (2006.01)
(52) U.S. Cl.
USPC ............................................................. 623/24

(58) Field of Classification Search
USPC ............................................................. 623/24
See application file for complete search history.

(56) References Cited

U.S. PATENT DOCUMENTS

| 4,743,019 A | 5/1988 | Lequeux |
| 5,888,213 A * | 3/1999 | Sears et al. ....................... 623/24 |
| 7,077,015 B2 | 7/2006 | Hayward et al. |

* cited by examiner

*Primary Examiner* — David H Willse
(74) *Attorney, Agent, or Firm* — Andrea Blecken; Stanford University

(57) ABSTRACT

The tactile feedback device of the preferred embodiments includes at least one skin contact pad; at least one actuator designed to move the at least one skin contact pad and attached to the at least one skin contact pad in a manner suitable to allow the actuator to move the at least one skin contact pad; a processor coupled to the actuator that executes a control logic and functions to control the movements of the at least one actuator; the control logic functions to determine the motions of the at least one actuator and is designed to move the at least one actuator in a manner that stretches the skin of the user. The tactile feedback device of the preferred embodiments has been designed to provide feedback to a user in a way that provides the user with information regarding a task that they are performing. The tactile feedback device of the preferred embodiments, however, may be used for any suitable purpose.

15 Claims, 10 Drawing Sheets

SKIN STRETCH TACTILE FEEDBACK DEVICE

RELATED APPLICATION

This application claims priority and other benefits from U.S. Provisional Patent Application Ser. No. 61/203,455, filed Dec. 22, 2008, entitled "Wearable Skin Stretch Device for Tactile Feedback". Its entire content is specifically incorporated herein by reference.

GOVERNMENT INTERESTS

Government Rights

This invention was made with Government support under contract IIS-0554188 awarded by the National Science Foundation. The Government has certain rights in this invention.

DESCRIPTION OF THE PREFERRED EMBODIMENTS

The following description of the preferred embodiments of the invention is intended to enable someone skilled in the prior art to make and use this invention, but is not intended to limit the invention to these preferred embodiments.

1. First Preferred Embodiment

Figure 1:
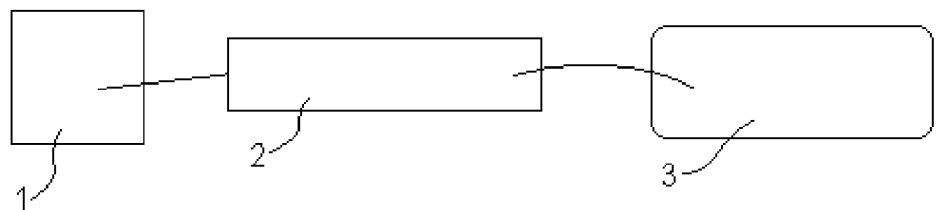
FIG. 1 is a schematic representation of the system of the first preferred embodiment.
Figure 2:
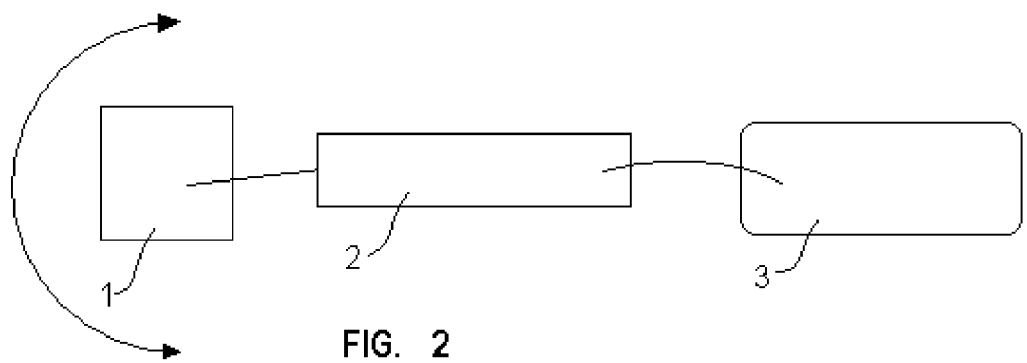
FIG. 2 is a schematic representation of the system of the first preferred embodiment wherein the actuator rotates the at least one skin contact pad.

As shown in FIG. 1, the tactile feedback device of the preferred embodiments includes at least one skin contact pad 1; at least one actuator 2 designed to move the at least one skin contact pad 1 and attached to the at least one skin contact pad 1 in a manner suitable to allow the actuator to move the at least one skin contact pad 1; a processor 3 coupled to the actuator that executes a control logic and functions to control the movements of the at least one actuator 2; the control logic functions to determine the motions of the at least one actuator 2 and is designed to move the at least one actuator 2 in a manner that stretches the skin of the user. The tactile feedback device of the preferred embodiments has been designed to provide feedback to a user in a way that provides the user with information regarding a task that they are performing. The tactile feedback device of the preferred embodiments, however, may be used for any suitable purpose.

Figure 3:
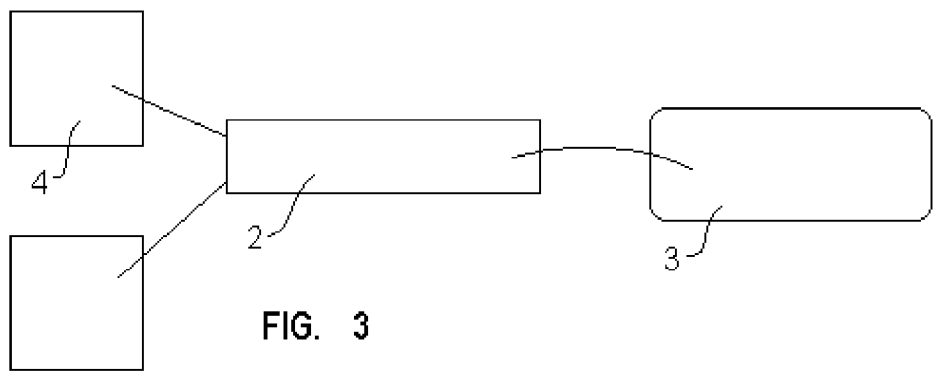
FIG. 3 is a schematic representation of the system of the first preferred embodiment wherein the system comprises at least two skin contact pads.
Figure 4A:
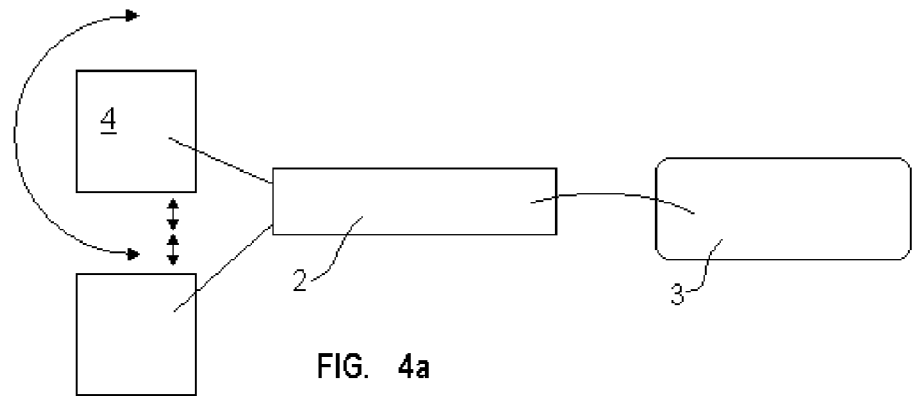
FIG. 4a is a schematic representation of the system of the first preferred embodiment wherein at least one of the skin contact pads both rotates and translates.
Figure 4B:
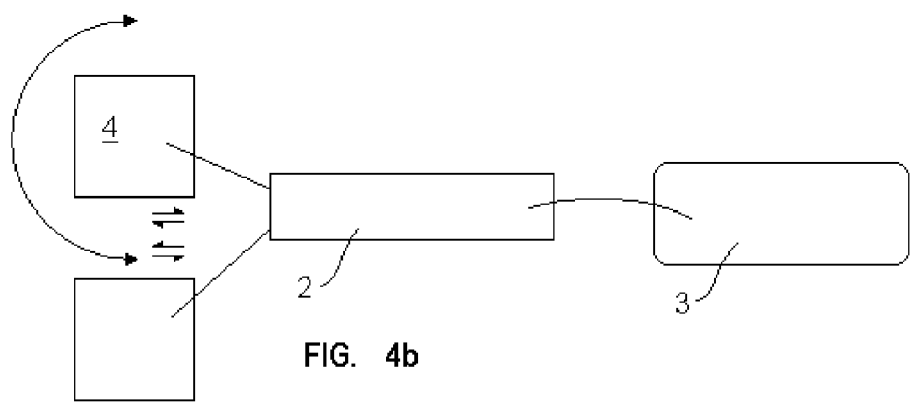
FIG. 4b is a schematic representation of the system of the first preferred embodiment wherein at least one of the skin contact pads both rotates and translates in a different mode.
Figure 5A:
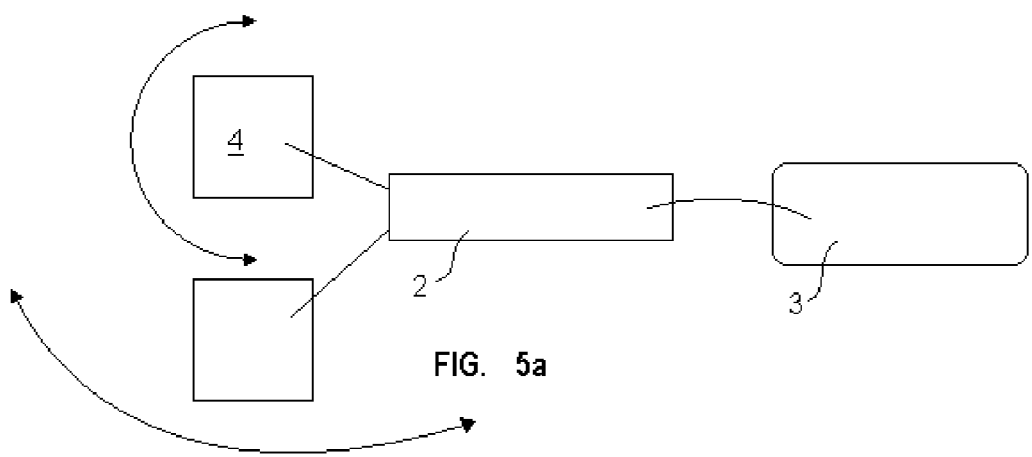
FIG. 5a is a schematic representation of the system of the first preferred embodiment wherein one of the at least two skin contact pads rotates about another of the at least two skin contact pads.
Figure 5B:
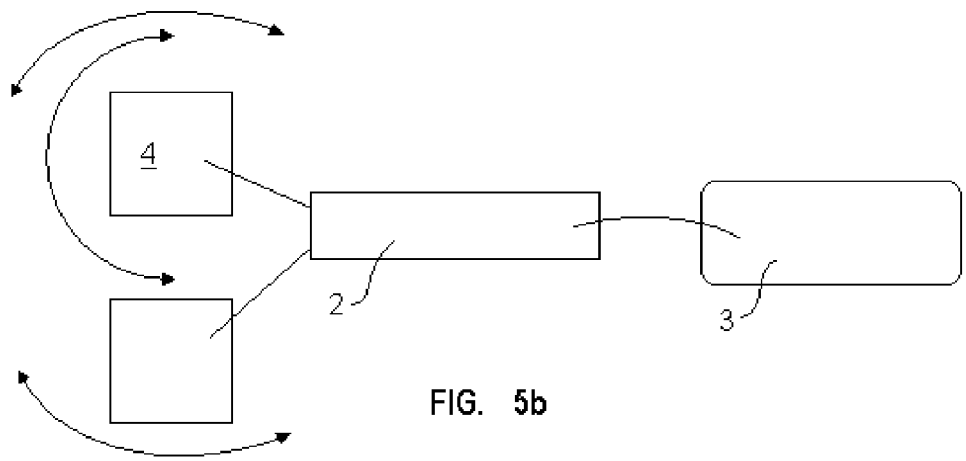
FIG. 5b is a schematic representation of the system of the first preferred embodiment wherein the at least two skin contact pads rotate about a fixed point.
Figure 6:
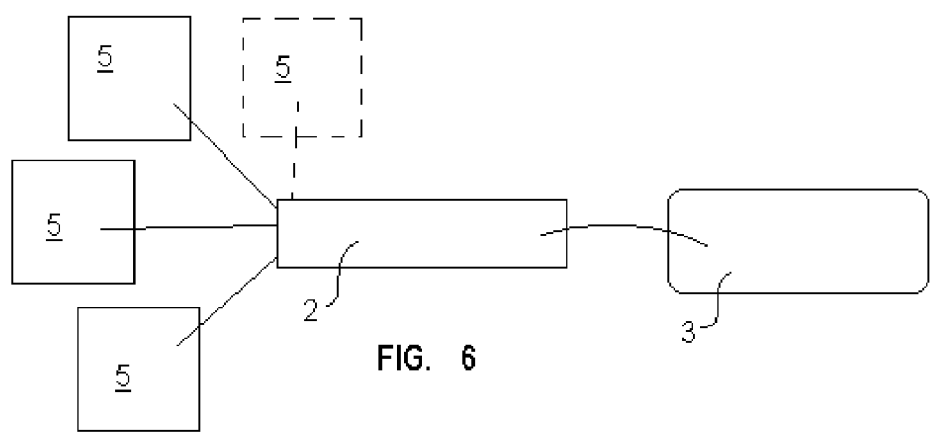
FIG. 6 is a schematic representation of the system of the first preferred embodiment wherein there are more than two skin contact pads.

As shown in FIGS. 2, 4a, 4b, 5a and 5b, the actuator functions to rotate, translate, or both rotate and translate the at least one skin contact pad 1. As shown in FIG. 3, at least two skin contact pads 4 are included when the actuator functions to create any sort of translational movement. As shown in FIG. 4a, the translation may include movement of the at least two skin contact pads 4 towards or away from one another. As shown in FIG. 4b, the translation may alternatively include movement of the at least two skin contact pads 4 parallel to one another and in opposite directions, such that they move tangentially to one another. Alternatively the translation may include a combination of both forms of movement. Preferably, the translational movement is created by rotating one of the at least two skin contact pads 4 around at least one other of the at least two skin contact pads 4, as shown in FIG. 5*a*. In a first variation, the translational movement can be created by rotating the at least two skin contact pads 4 around a fixed point, as shown in FIG. 5*b*. Alternatively, the translational movement can be created by linear motion or any other suitable means. As shown in FIG. 6, the tactile feedback device may alternatively include more than two skin contact pads 5. The skin contact pads may, however, be moved in any mode or combination of modes suitable for stretching the user's skin 7.

Figure 7A:
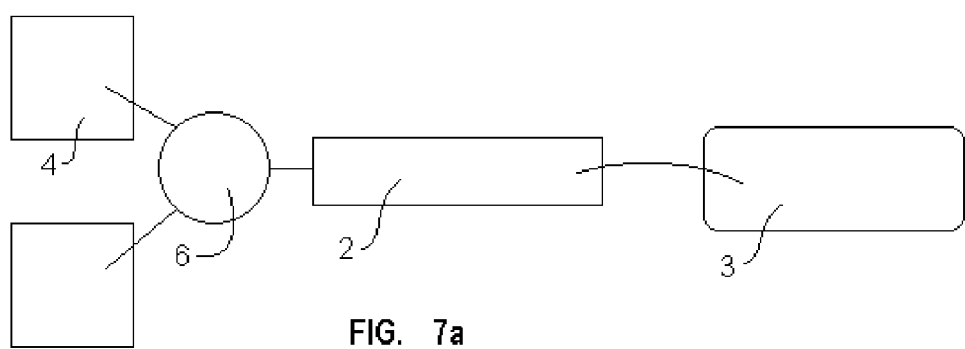
FIG. 7a is a schematic representation of the system of the first preferred embodiment wherein the system further comprises a transmission coupled to the at least one actuator and coupled to the at least two skin contact pads.
Figure 7B:
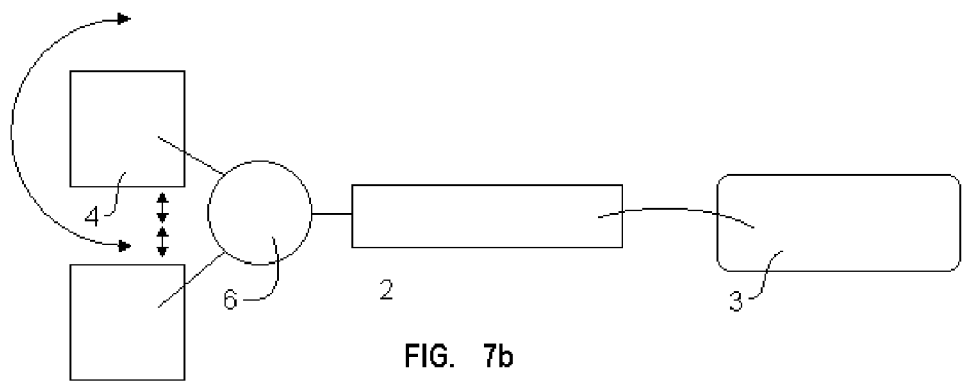
FIG. 7b is a schematic representation of the system of the first preferred embodiment wherein the system further comprises a transmission adapted to transfer the motion of the at least one actuator into the motion of the at least two skin contact pads, preferably the motion is rotation and translation.
Figure 7C:
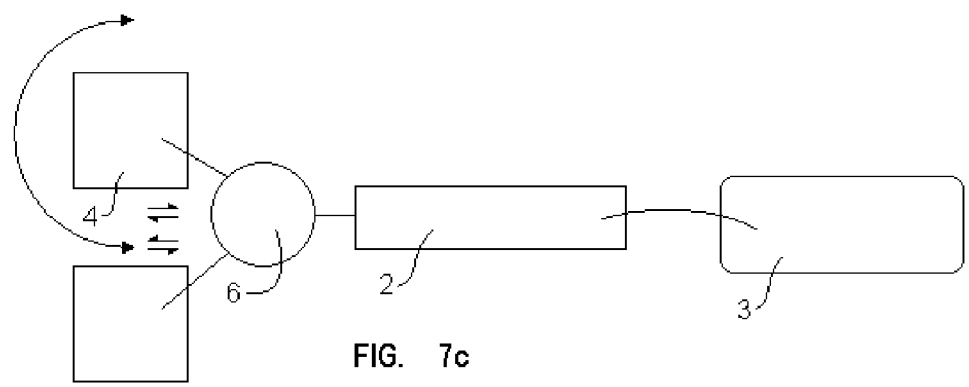
FIG. 7c is a schematic representation of the system of the first preferred embodiment wherein the system further comprises a transmission adapted to transfer the motion of the at least one actuator into the motion of the at least two skin contact pads, preferably the motion is rotation and translation.

As shown in FIG. 7*a*, the actuator is preferably coupled to a transmission 6, and the transmission 6 is preferably coupled to the at least two skin contact pads 4. As shown in FIGS. 7*b* and 7*c*, the transmission 6 is designed to transfer the motion of the at least one actuator 2 to the at least two skin contact pads 4, and is preferably designed to transfer the motion of the at least one actuator 2 into the rotation and translation of at least one of the at least two skin contact pads 4. However, the transmission 6 may be connected to only one skin contact pad, or any other number of skin contact pads. The transmission 6 may, alternatively, be designed to transfer the movement of the actuator into any form of skin contact pad motion.

In a first preferred variation, the transmission 6 is a cable transmission 6. In a second preferred variation, the transmission 6 is a geared transmission 6. In a third preferred variation, the transmission 6 is a combination cable and geared transmission 6. In an alternative variation, the actuator is coupled to a cable transmission 6 which is coupled to a geared transmission 6, and the geared transmission 6 is coupled to the at least two skin contact pads 4. However, the transmission 6 can be any suitable design capable of transferring the actuator movement into the required movement of the at least one skin contact pad 1.

Figure 8:
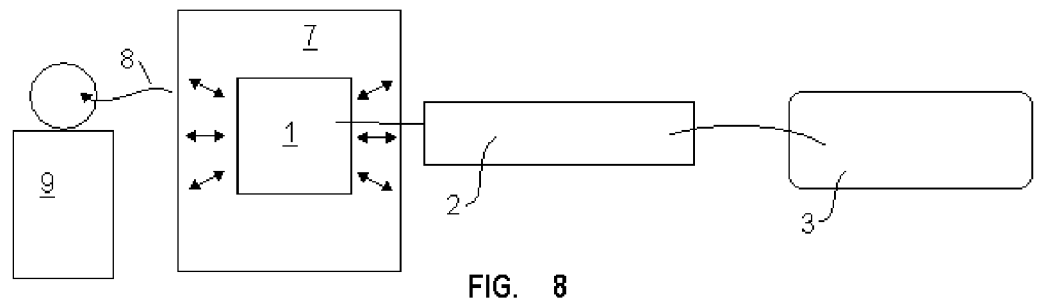
FIG. 8 is a schematic representation of the system of the first preferred embodiment wherein the system stretches the user's skin to provide feedback to the user.

The control logic of the tactile feedback device includes an algorithm that determines how to move the at least one skin contact pad 1 in a way that stretches the user's skin 7 and provides feedback 8 to the user 9, as shown in FIG. 8. Preferably the control logic determines a desired position of the at least one skin contact pad 1 to create the desired feedback 8. Preferably the control logic includes calculating the difference between the desired position of the at least one skin contact pad 1 and the actual position of the at least one skin contact pad 1, and preferably the control logic uses this calculated difference to refine the motion of the at least one actuator 2 and the at least one skin contact pad 1. Preferably the control logic also calculates the derivative of the difference between the actual and desired positions of the at least one skin contact pad 1, and the control logic preferably takes this information into account when determining the speed of the at least one actuator 2 and the at least one skin contact pad 1.

Figure 9:
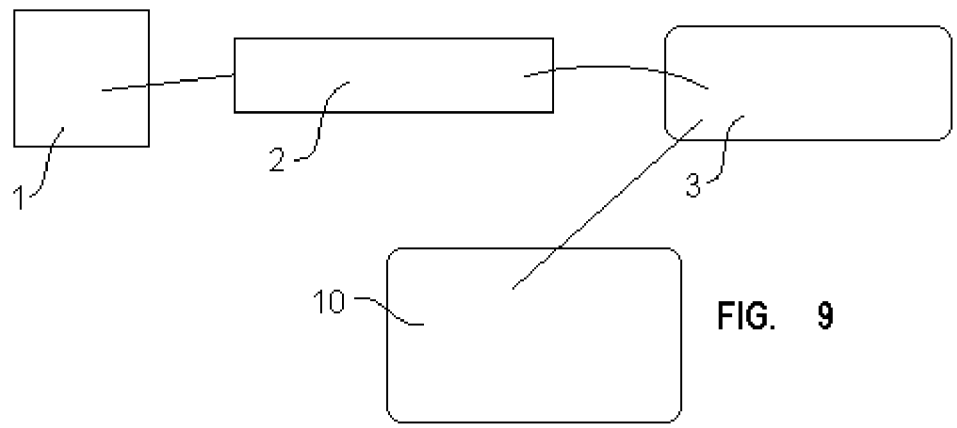
FIG. 9 is a schematic representation of the system of the first preferred embodiment wherein the system further comprises a sensor.

As shown in FIG. 9, the tactile feedback device preferably includes a sensor 10 coupled to the processor 3, and the processor 3 is designed to take into account the output of the sensor 10 when calculating how to stretch the user's skin 7 and how to move the at least one actuator 2. The sensor 10 is preferably a position sensor 10 or a motion sensor 10. In one preferred variation, the sensor 10 is an accelerometer. However it may be any suitable type of sensor 10 which can be used to influence or determine the feedback given to the user. Preferably, the processor 3 instructs the actuator to make one or more of: the amount of skin stretch, the direction of skin stretch, and the speed of skin stretch relative to the output of the sensor 10. The control logic preferably takes into account the output of the sensor 10 when determining the desired position of the at least one skin contact pad 1. The desired position of the at least one skin contact pad 1 may, however, be determined by any suitable means. The tactile feedback device may also include any number of sensors or none at all.

Figure 10:
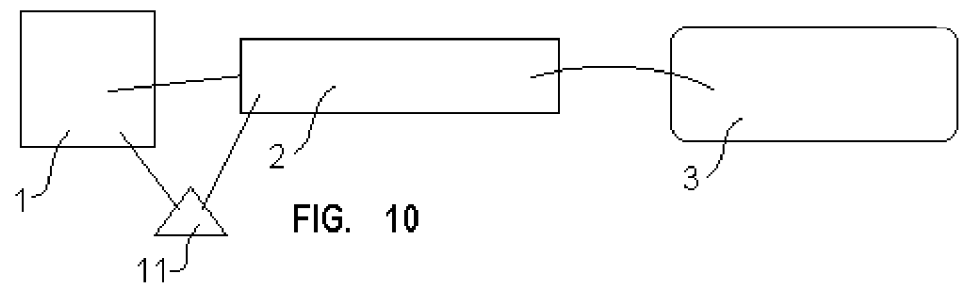
FIG. 10 is a schematic representation of the system of the first preferred embodiment wherein the system further comprises a rotational sensor.

As shown in FIG. 10, the tactile feedback device preferably includes a rotational sensor 11 coupled to the processor 3 and to the at least one skin contact pad 1. The processor 3 is preferably designed to use the output of the rotational sensor 11 to monitor the position of the at least one skin contact pad 1. The processor 3 is preferably further designed to use the rotational sensor 11 to refine the motion of the at least one actuator 2 and the at least one skin contact pad 1. The processor 3 refines the motion of the at least one actuator 2 and the at least one skin contact pad 1 by using the control logic, wherein the actual position of the at least one skin contact pad 1 is preferably determined by the rotational sensor 11. In one variation, the actual position of the at least one skin contact pad 1 is assumed by taking into account the history of the instructions given to the actuator by the processor 3. The actual position of the at least one skin contact pad 1 may, however, be determined by any suitable means or may not be determined. The rotational sensor 11 is preferably an encoder or a hall effect sensor, though it may be any suitable type of rotational sensor 11.

Figure 11:
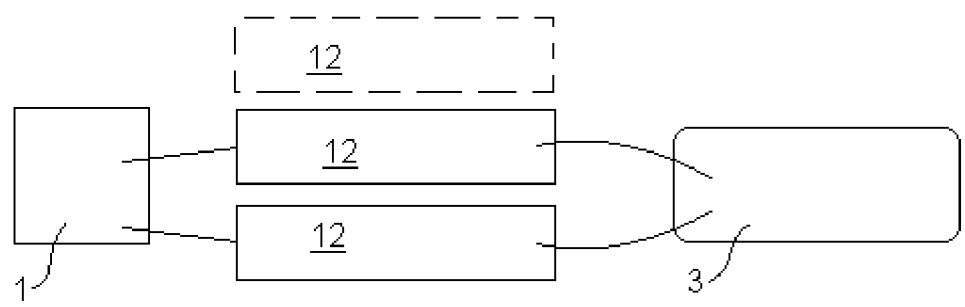
FIG. 11 is a schematic representation of the system of the first preferred embodiment wherein the system comprises more than one actuator.
Figure 12A:
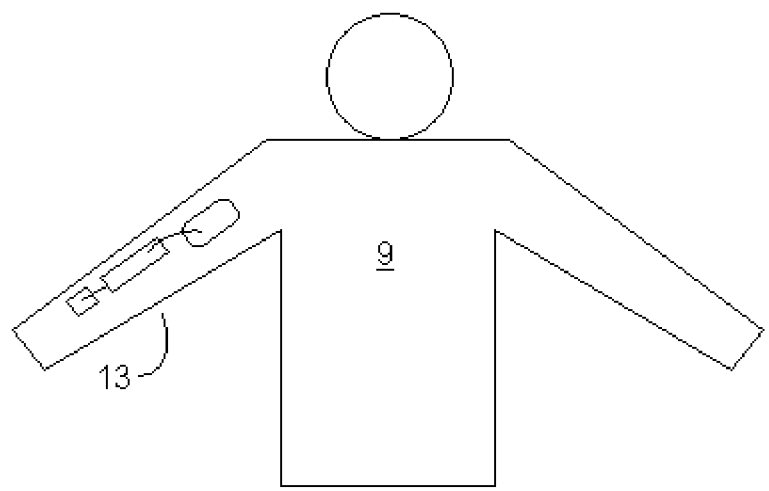
FIG. 12a is a schematic representation of the system of the first preferred embodiment wherein the system is mounted on the user's arm.
Figure 12B:
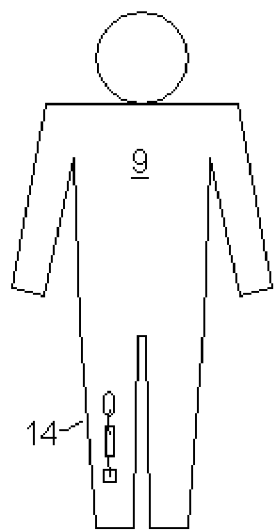
FIG. 12b is a schematic representation of the system of the first preferred embodiment wherein the system is mounted on the user's leg.
Figure 12C:
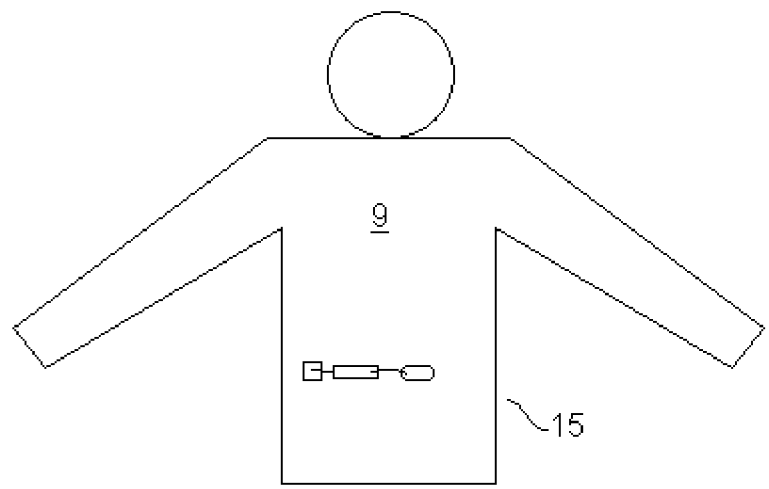
FIG. 12c is a schematic representation of the system of the first preferred embodiment wherein the system is mounted on the user's torso.
Figure 12D:
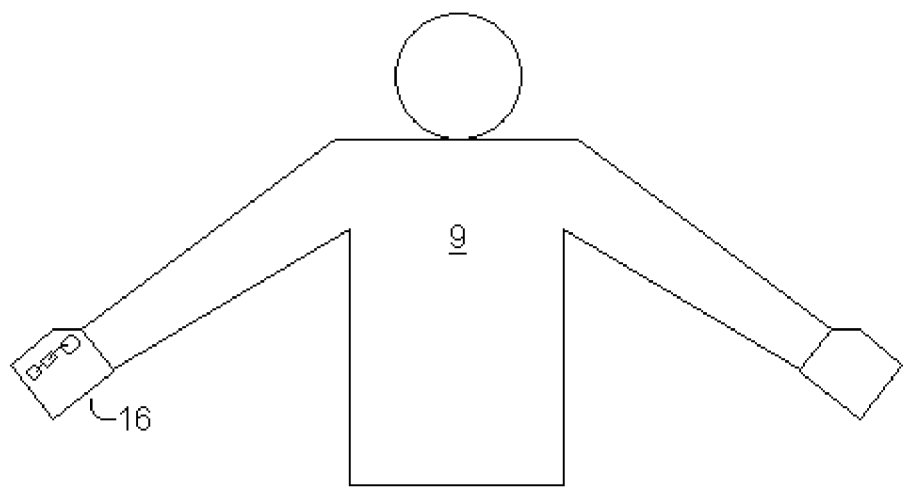
FIG. 12d is a schematic representation of the system of the first preferred embodiment wherein the system is mounted on the user's hand.

As shown in FIG. 1, the at least one actuator 2 is preferably one actuator. Preferably the actuator is a piezoelectric motor, however the actuator can be any suitable type of actuator. As shown in FIG. 11, in one variation the tactile feedback device includes more than one actuator 12.

As shown in FIGS. 12*a*, 12*b*, 12*c*, and 12*d*, the tactile feedback device is preferably mounted on any one of the user's arm 13*s*, the user's leg 13*s*, the user's torso 13 and the user's hand 13*s*. The tactile feedback device may also be mounted on any other suitable portion of the user's body where it can stretch the user's skin 7.

2. Second Preferred Embodiment

Figure 13:
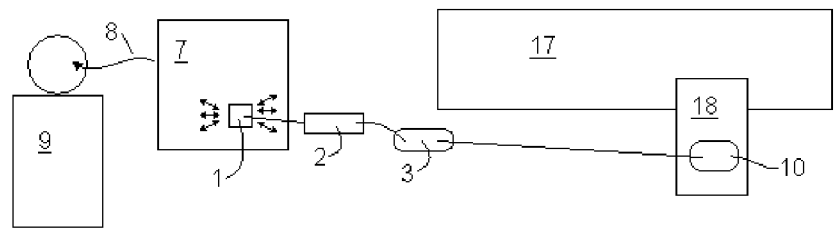
FIG. 13 is a schematic representation of the system of the second preferred embodiment.

As shown in FIG. 13, the tactile feedback device of the second preferred embodiment includes a prosthetic body part 17; at least one moving component 18 coupled to the prosthetic body part 17; at least one sensor 10 coupled to the at least one moving component 18 and designed to sense information regarding the at least one moving component 18; a tactile feedback device coupled to the at least one sensor 10 and designed to provide feedback to the user based on the sensed information regarding the at least one moving component 18. The tactile feedback device includes at least one skin contact pad 1; at least one actuator 2 coupled to the at least one skin contact pad 1 and designed to move the at least one skin contact pad 1; a processor 3 designed to control the at least one actuator 2 and designed to implement a control logic; the control logic is designed to determine how the actuator is moved and is designed to move the actuator in a manner that stretches the skin of the user and provides the user with feedback. The information regarding the at least one moving component 18 includes one or more of: the motion, velocity, or position of the at least one moving component 18, the force on the at least one moving component 18, and the force exerted by the at least one moving component 18.

3. Third Preferred Embodiment

Figure 14:
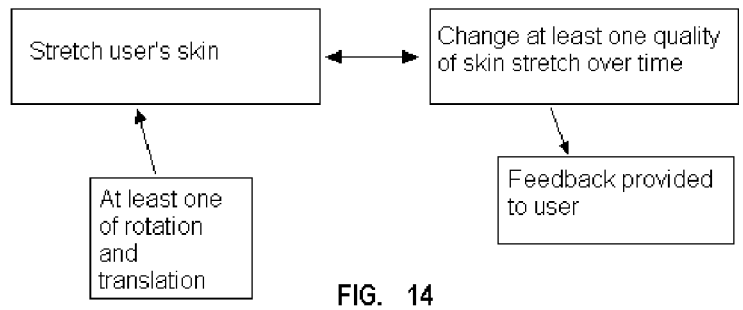
FIG. 14 is a flow chart representation of the method of the third preferred embodiment.

As shown in FIG. 14, the method of the third preferred embodiment includes (a) stretching a user's skin by the use of one or more of the following: the rotation of at least one skin contact pad and the translation of at least two skin contact pads; and (b) changing at least one quality of the skin stretch over time, where the change in skin stretch is designed to provide feedback to a user.

Figure 15:
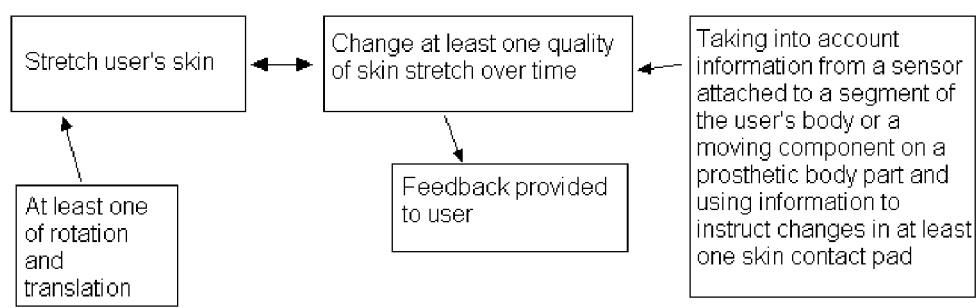
FIG. 15 is a flow chart representation of the method of the third preferred embodiment wherein the method further comprises taking into account information from a sensor.

As shown in FIG. 15, the method preferably includes taking into account information from a sensor when deciding how to change the motion of the at least one skin contact pad. Preferably the sensor is attached to at least one segment of the user's body or at least one moving component on a prosthetic body part, however it can be mounted in any way that allows it to gather information on at least one segment of the user's body or at least one moving component of a prosthetic body part. Preferably the sensor is either a position sensor, a motion sensor, or both. In one variation more than one sensor may be used. Any suitable type of information, both from sensors and without sensors, may, however, be used to decide how to change the motion of the at least one skin contact pad.

Figure 16:
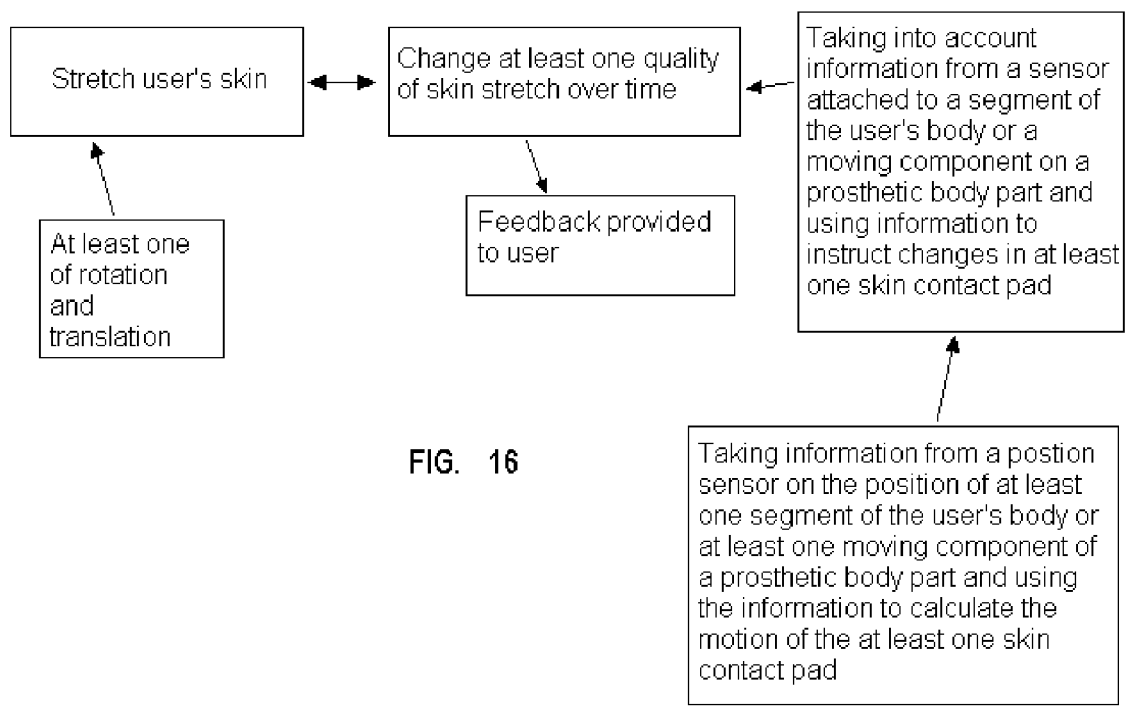
FIG. 16 is a flow chart representation of the method of the third preferred embodiment wherein the method further comprises taking information from a position sensor.

As shown in FIG. 16, the method preferably includes taking information on the position of at least one segment of a user's body or at least one moving component of a prosthetic body part from a position sensor and calculating the motion of the at least one skin contact pad using the position information such that the motion is relative to the position information. The motion of the at least one skin contact pad is then instructed taking into account the motion calculated by this process. The motion of the at least one skin contact pad may, however, be calculated and instructed using any suitable means that create suitable feedback.

Figure 17:
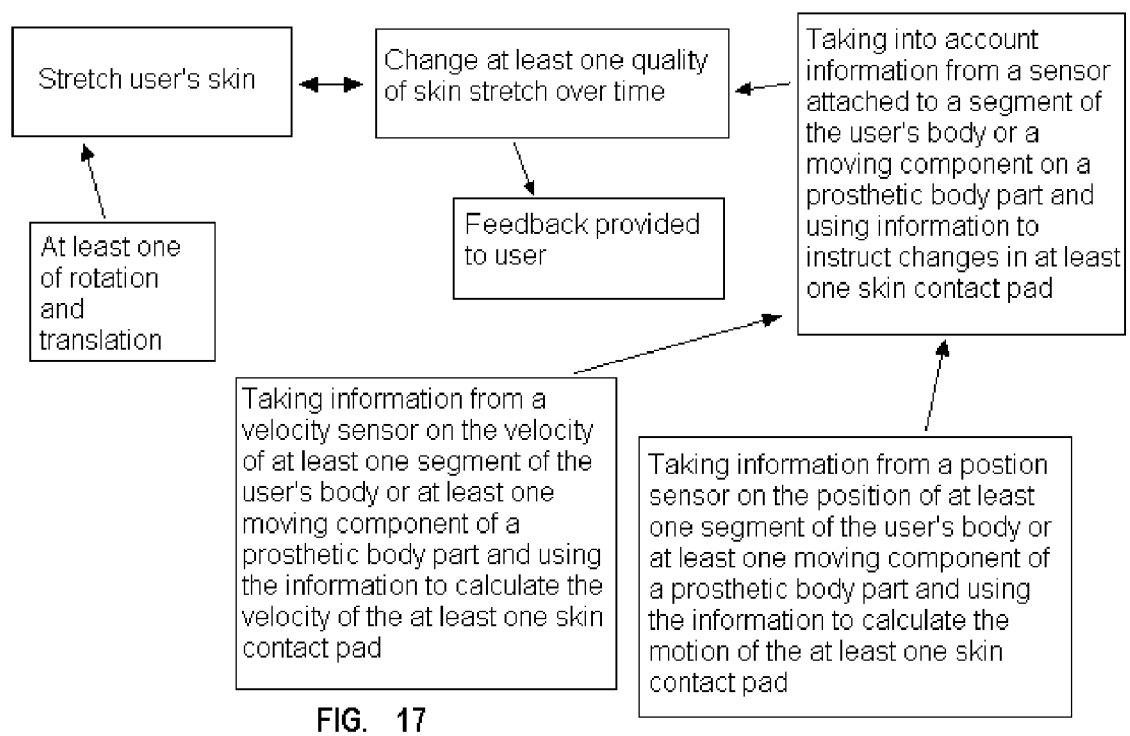
FIG. 17 is a flow chart representation of the method of the third preferred embodiment wherein the method further comprises taking information from a motion sensor.

As shown in FIG. 17, the method preferably includes taking information on the velocity of at least one segment of the user's body or at least one moving component of a prosthetic body part from a motion sensor and calculating the velocity of the at least one skin contact pad using the velocity information such that the velocity is relative to the velocity information. The velocity of the at least one skin contact pad is then instructed taking into account the velocity calculated by this process. The velocity of the at least one skin contact pad may, however, be calculated and instructed using any suitable means that create suitable feedback.

The method may, however, provide feedback to the user in response to any situation and for any purpose. In one variation, the method provides feedback relative to the actions of a vehicle the user is controlling. In another variation, the method provides feedback to the user relative to an abstract task a user is performing, including a task on a computer; however the task may be of any type where suitable advantage may be gained from providing feedback.

As a person skilled in the prior art will recognize after examination of the previous detailed description and the figures and claims, modifications and changes may be made to the preferred embodiments of the invention without departing from the scope of the invention as defined in the following claims.

We claim:

1. A portable skin stretch tactile feedback device for providing a user proprioceptive information, said device comprising at least two bidirectionally rotating skin contact pads for inducing a rotational skin stretch with shear strain for indicating position and motion of user's body parts; actuators coupled to said skin contact pads and adapted for controlling the rotating of said skin contact pads; a processor for controlling the actuators and for implementing a control logic wherein the control logic determines degree and direction of rotation of said skin contact pads.

2. The tactile feedback device in accordance to claim 1, wherein the skin contact pads rotate in a fixed point position.

3. The tactile feedback device in accordance to claim 1, wherein the skin contact pads rotate freely.

4. The tactile feedback device in accordance to claim 1, wherein the control logic comprises an algorithm that determines degree and direction of rotation of said skin contact pads.

5. The tactile feedback device in accordance to claim 4, wherein the skin contact pads move in the same direction.

6. The tactile feedback device in accordance to claim 4, wherein the skin contact pads move in opposite directions.

7. The tactile feedback device of in accordance to claim 1, further comprising a position sensor and a motion sensor coupled to the processor for modulating said actuators to stretch the user's skin relative to the output of the position sensor and the motion sensor.

8. The tactile feedback device of in accordance to claim 7, wherein the motion sensor is an accelerometer.

9. The tactile feedback device in accordance to claim 1, whereby the device is mounted on any of the user's arms, legs, torso and hands.

10. The tactile feedback device in accordance to claim 1, further comprising a rotational sensor that is connected to the skin contact pads and coupled to the processor for monitoring and modulating the position of the skin contact pads.

11. The tactile feedback device in accordance to claim 1, wherein the actuators are piezoelectric motors.

12. A method of providing a user with information indicating position and motion of the user's body parts, said method comprising detecting and tracking said user's motions by employing at least two bidirectionally rotating skin contact pads for inducing a rotational skin stretch with shear strain, whereby the rotating of said skin contact pads is controlled by actuators and whereby said actuators are controlled by a processor that implements a control logic for determining degree and direction of rotation of said skin contact pads.

13. The method in accordance to claim 12, wherein said information is utilized for motion training and motion adjustment in physical exercise.

14. The method in accordance to claim 12, wherein said information is utilized for motion training and motion adjustment to facilitate physical rehabilitation.

15. The method in accordance to claim 12, wherein said information is utilized for motion tracking of a prosthetic body part.

* * * * *